US007702467B2

(12) United States Patent
Duffy

(10) Patent No.: US 7,702,467 B2
(45) Date of Patent: Apr. 20, 2010

(54) MOLECULAR PROPERTY MODELING USING RANKING

(75) Inventor: Nigel P. Duffy, San Francisco, CA (US)

(73) Assignee: Numerate, Inc., San Bruno, CA (US)

(*) Notice: Subject to any disclaimer, the term of this patent is extended or adjusted under 35 U.S.C. 154(b) by 1263 days.

(21) Appl. No.: 11/172,215

(22) Filed: Jun. 29, 2005

(65) Prior Publication Data
US 2005/0288868 A1 Dec. 29, 2005

Related U.S. Application Data

(60) Provisional application No. 60/584,819, filed on Jun. 29, 2004, provisional application No. 60/584,820, filed on Jun. 29, 2004.

(51) Int. Cl.
*G01N 33/48* (2006.01)
*G01N 31/00* (2006.01)
(52) U.S. Cl. .......................... 702/19; 702/22
(58) Field of Classification Search .................. None
See application file for complete search history.

(56) References Cited

U.S. PATENT DOCUMENTS

| 5,463,564 | A |  | 10/1995 | Agrafiotis et al. |
| 5,574,656 | A |  | 11/1996 | Agrafiotis et al. |
| 5,684,711 | A |  | 11/1997 | Agrafiotis et al. |
| 5,901,069 | A |  | 5/1999 | Agrafiotis et al. |
| 6,081,766 | A | * | 6/2000 | Chapman et al. ............... 702/27 |
| 6,421,612 | B1 |  | 7/2002 | Agrafiotis et al. |
| 6,434,490 | B1 |  | 8/2002 | Agrafiotis et al. |
| 6,678,619 | B2 |  | 1/2004 | Lobanov et al. |
| 6,691,045 | B1 |  | 2/2004 | Labute |
| 6,834,239 | B2 |  | 12/2004 | Lobanov et al. |
| 2003/0073128 | A1 |  | 4/2003 | Egan et al. |

FOREIGN PATENT DOCUMENTS

| EP | 1326183 A1 | 7/2003 |
| WO | WO-02082329 A2 | 10/2002 |
| WO | WO-02082329 A3 | 10/2002 |

OTHER PUBLICATIONS

Brusic et al. "Prediction of promiscuous peptides that bind HLA class I molecules," Immunology and Cell Biology (2002) vol. 80, pp. 280-285.*
Carlsen, L., et al., "Improving the Predicting Power of Partial Order Based QSARs through Linear Extensions", *Journal of Chemical Information and Computer Science*, 42 (4), American Chemical Society,(Jul. 2002),806-811.
Manly, C. J., et al., "The Impact of Informatics and Computational Chemistry on Synthesis and Screening", *Drug Discovery Today*, 6 (21), Elsevier Science Ltd,(Jan. 2001),1101-1110.
Taskinen, J., et al., "Prediction of Physicochemical Properties Based on Neural Network Modelling", *Advanced Drug Delivery Reviews*, 55 (9), www.sciencedirect.com,(Sep. 12, 2003),1163-1183.
Wang et al. "1-(5-Chloro-2-alkoxypheny)-3-(5-cyanopyrazi-2-yl)ureas as Potent and Selective Inhibitors of Chk1 Kinase: Synthesis, Preliminary SAR, and Biological Activities." *Journal of Medical Chemistry*. 2005 vol. 48(9): pp. 33118-3121.
Lerche et al. "A Comparison of Partial Order Technique with Three Methods of Multi-Criteria Analysis for Ranking of Chemical Substances." *J. Chem. Inf. Comput. Sci. 2002* vol. 42: pp. 1086-1098.
Lebanon et al. "Conditional Models on the Ranking Poset." *NIPS*. Dec. 2002 vol. 15: pp. 415-422.
Collins et al. "Convolution Kernels for Natural Language." *NIPS*. Dec. 2001 vol. 14: pp. 625-632.
Roark et al. "Corrective Language Modeling for Large Vocabulary ASR with the Perceptron Algorithm." *IEEE International Conference on Acoustics. Speech, and Signal Processing*. May 2004 vol. 1(17-21): pp. 749-752.
Lebanon et al. "Cranking: Combining Rankings Using Conditional Probability Models on Permutations." *ICML* 2002: pp. 363-370.
Roark et al. "Discriminative Language Modeling with Conditional Random Fields and the Perceptron Algorithm." *ACL* 2004: pp. 47-54.
Michael Collins. "Discriminative Reranking for Natural Language Parsing." *ICML*. 2000: pp. 175-182.
Collins et al. "Discriminative Reranking for Natural Language Parsing." *Computational Linguistics*. 2005 vol. 31(1): pp. 25-69.
Michael Collins. "Discriminative Training Methods for Hidden Markov Models: Theory and Experiments with Perceptron Algorithms." *Proceedings of the Conference on Empirical Methods in Natural Language Processing*. Jul. 2002: pp. 1-8.
Freund et al. "An Efficient Boosting Algorithm for Combining Preferences." *ICML*. 1998: pp. 170-178.
Brüggemann et al. "Estimation of Averaged Ranks by a Local Partial Order Model." *J. Chem. Inf. Comput. Sci.* 2004 vol. 44(2): pp. 618-625.
Lerche et al. "Improved Estimation of the Ranking Probabilities in Partial Orders Using Random Linear Extensions by Approximation of the Mutual Ranking Probability." *J. Chem. Inf. Comput. Sci.* 2003 vol. 43(5): pp. 1471-1480.
Collins et al. "Incremental Parsing with the Perceptron Algorithm." *ACL* 2004: pp. 111-118.
Cohen et al. "Learning to Order Things." *Journal of Artificial Intelligence Research*. 1999 vol. 10: pp. 243-270.

(Continued)

*Primary Examiner*—John S Brusca
*Assistant Examiner*—Anna Skibinsky
(74) *Attorney, Agent, or Firm*—Mosier IP Law Group

(57) ABSTRACT

Methods and articles of manufacture for modeling molecular properties using data regarding the partial orderings of compound properties, or by considering measurements of compound properties in terms of partial orderings are disclosed. One embodiment provides for constructing such partial orderings from data that is not already in an ordered form by processing training data to produce a partial ordering of the compounds with respect to a property of interest. Another embodiment of the invention may process the modified training data to construct a model that predicts the property of interest for arbitrary compounds.

28 Claims, 7 Drawing Sheets

OTHER PUBLICATIONS

Herbrich et al. "Learning Preference Relations for Information Retrieval." *ICML*. 1998: pp. 80-84.

Weston et al. "Machine Learning Approaches to Protein Ranking: Discriminative, Semi-Supervised, Scalable Algorithms." *Max Planck Institute for Biological Cybemetics*. Jun. 2003 vol. 111(9): pp. 1-9.

Collins et al. "New Ranking Algorithms for Parsing and Tagging: Kernels over Discrete Structures, and the Voted Perceptron." *ACL*. pp: 263-270., (2001).

Collins et al "Parsing with a Single Neuron: Convolution Kernels for Natural Language Problems." *Technical Report*. University of California, Santa Cruz, 2001 http://citeseer.ist.psu.edu/collins01parsing.html.

Carlsen et al. "Partial Order Ranking-Based QSAR's: Estimation of Solubilities and Octanol-Water Partitioning." *Chemosphere*. 2001 vol. 43: pp. 295-302.

Crammer et al. "Pranking with Ranking." *Advances in Neural Information Processing Systems*. 2002 vol. 14: pp. 641-647.

Warmuth et al. "Support Vector Machines for Active Learning in the Drug Discovery Process." University of California, Santa Cruz. *Dissertation Proposal*. Dec. 2002 vol. 43(2): pp. 667-673.

Hedfors et al. "Thyroid Receptor Ligands. 3. Design and Synthesis of 3,5-Dihalo-4-alkoxyphenylalkanoic Acids as Indirect Antagonists of the Thyroid Hormone Receptor." *Journal of Medicinal Chemistry*. 2005 vol. 48(9): pp. 3114-3117.

Provost et al. "Tree Induction for Probability-Based Ranking." *Machine Learning*. 2003 vol. 52(3): pp. 199-215.

\* cited by examiner

MOLECULAR PROPERTY MODELING USING RANKING

CROSS-REFERENCE TO RELATED APPLICATIONS

This application claims priority to U.S. provisional patent application Ser. No. 60/584,819, filed Jun. 29, 2004, and to U.S. Provisional patent application Ser. No. 60/584,820, filed Jun. 29, 2004, both of which are incorporated by reference herein in their entirety.

This application is also related to the following: (1) U.S. Pat. No. 6,571,226, Issued May 27, 2003, (2) U.S. patent application Ser. No. 11/074,587, filed on Mar. 8, 2005, (3) U.S. patent application Ser. No. 10/449,948, filed on May 30, 2003, now abandoned; (4) U.S. patent application Ser. No. 10/452,481, filed on May 30, 2003, and (5) U.S. patent application Ser. No. 11/172,216, filed on even date herewith entitled "Estimating the Accuracy of Molecular Properties Models and Predictions", Now U.S. Pat. No. 7,194,359. Each of the aforementioned patent and patent applications are incorporated by reference herein in their entirety.

BACKGROUND OF THE INVENTION

1. Field of the Invention

Embodiments of the present invention generally relate to machine learning techniques and, more particularly, to a method, article of manufacture and apparatus for modeling molecular properties using ranked data and ranking algorithms.

2. Description of the Related Art

Many industries use machine learning techniques to construct predictive models of relevant phenomena. For example, machine learning applications have been developed to detect fraudulent credit card transactions, predict creditworthiness, or recognize words spoken by an individual. Machine learning techniques have also been applied to create predictive models of chemical and biological systems. Generally, machine learning techniques are used to construct a software application that improves its ability to perform a task as it analyzes more data related to the task. Often, the task is to predict an unknown attribute or quantity from known information (e.g., credit risk predictions based on prior lending history and payment performance), or to classify an object as belonging to a particular group (e.g., speech recognition software that classifies speech into individual words). Typically, a machine learning application improves its performance using a set of training examples. Each training example may include an example of an object, along with a value for the otherwise unknown classification of the object. By processing a set of training examples that include both an object and a classification for the object, the model "learns" what attributes or characteristics of the object are associated with a particular classification. This "learning" may then be used to predict the attribute or to predict a classification for other objects. For example, speech recognition software may be trained by having a user recite a pre-selected paragraph of text. By examining the attributes of the recited text, the software learns to recognize the words spoken by the individual speaker.

In the fields of bioinformatics and computational chemistry, machine learning applications have been used to develop models of various molecular properties. Oftentimes, such models are built in an attempt to predict whether a particular molecule will exhibit the property being modeled. For example, models may be developed to predict biological properties such as pharmacokinetic or pharmacodynamic properties, physiological or pharmacological activity, toxicity or selectivity. Other examples include models that predict chemical properties such as reactivity, binding affinity, or properties of specific atoms or bonds in a molecule, e.g. bond stability. Similarly, models may be developed that predict physical properties such as the melting point or solubility of a substance. Further, molecular models may also be developed that predict properties useful in physics-based simulations such as force-field parameters or the free energy states of different possible conformations of a molecule.

The training examples used to train a molecular properties model each typically include a description for a molecule (e.g., the atoms in a particular molecule along with the bonds between them) and data regarding the property of interest for the molecule. Collectively, the training examples are commonly referred to as a "training set" or as "training data." Data regarding the property of interest typically takes one of two forms: (i) a value from a continuous range (e.g., the solubility of a molecule at a solute temperature), or (ii) a label asserting presence or absence of the property of interest relative to the molecule included in the training example. In either case, the training examples measure the property of interest relative only to the molecule included in a particular training example.

Using training data in either form has often, however, proved to be ineffective in training molecular properties models with a useful degree of predictive power. This may occur due to problems with the quality of the training data. First, consider a scenario where the data is a numerical value representing a measurement of the property of interest over a continuous range. The measurement values available for a particular molecule frequently differ depending on the data source. For example, measurements obtained from one lab or using one experimental protocol may consistently assign higher values for a property of interest to a particular molecule than others. These differences often lead to inconsistent values for the property of interest being reported for the same molecule. Additionally, even measurements obtained under "identical" experimental conditions may have enough experimental uncertainty or noise that it becomes unreasonable to assign a precise numerical value to the property of interest. One reasonable observation under these circumstances may be that if the difference in, or relative magnitude of, measurements reported for two different molecules is large enough, then one molecule may be said to have "more" of the property than the other.

Measurements for a set of molecules may be either relative or absolute. For example, this is commonly encountered in molecular modeling calculations where the ranking of molecules based on the calculation of absolute binding energies can be less accurate than the ranking of compounds based on relative calculated binding energies.

Training examples that use a label asserting the presence or absence of the property of interest have also proven to be of limited value in training a molecular properties model. Oftentimes, such data has a large bias in that the data is predominantly of one label. (e.g., nearly all of the molecules are "inactive" for the property of interest). In this case, it is easy to obtain a model with high accuracy; the model simply predicts the predominant label (e.g., always predict that a molecule will not have the property of interest). This model, however, is not particularly useful, as it makes the same prediction for every molecule.

Generally, models built from data will not predict the property of interest with perfect accuracy for all molecules, and there will be some errors. For binary valued data (i.e. training examples that use a label asserting the presence or absence of a property) these errors consist of false positives (i.e. molecules falsely predicted to have the property of interest), or false negatives (i.e. molecules falsely predicted to not have the property of interest). These types of errors have different costs, (e.g., in a diamond mine it is far more expensive to falsely predict that a diamond is dirt than it is to predict that dirt is a diamond). In biological and pharmaceutical applications, however, it can be very difficult to assign relative values to false positives and false negatives and so it becomes very difficult to trade them off.

As these examples illustrate, it is often easier (and more accurate) to consider the ordering of two molecules relative to a certain property than it is to assert an absolute value for the property for a single molecule. Existing molecular property modeling techniques, however, are not capable of using such ordering information, nor are they capable of dealing with bias in the data or of constructing reasonable models without knowing the optimal trade-off between false positives and false negatives. Accordingly, there is a need for improved methods and apparatus for modeling molecular properties.

SUMMARY OF THE INVENTION

Embodiments of the invention provide methods, apparatus, and articles of manufacture for training a molecular properties model. Specifically, embodiments of the invention provide novel techniques for training molecular properties models that order (or rank) sets of molecules with respect to a property of interest. Embodiments of the invention provide novel techniques for generating ranked training data used to train a molecular properties model. Further, embodiments of the invention provide novel techniques for training molecular properties models based on data provided in a ranked form. Further, embodiments of the present invention provide novel techniques for training molecular properties models that order sets of molecules relative to a property of interest based on data that is not provided in a ranked form. Further, embodiments of the present invention provide novel techniques for dealing with the bias in training data and for constructing an accurate model despite not knowing the trade-off between false positives and false negatives a priori. One embodiment of the invention provides a method for generating a pseudo-partial ordering of ranked pairs of molecules, used to train a molecular properties model. The method generally includes obtaining a set of property measurements for a plurality of molecules, wherein each measurement assigns a value for a property of interest relative to a single molecule, selecting pairs of molecules from the plurality, wherein a first and second molecule, in a pair of molecules, are ordered relative to one another and the property of interest, and combining the selected pairs of molecules to form the pseudo-partial ordering of ranked pairs.

Another embodiment provides a method for training a molecular properties model that includes obtaining a pseudo-partial ordering of ranked pairs, wherein each ranked pair includes at least a representation of a first and second molecule, ordered relative to one another and a property of interest, and generating a representation of the molecules included in the pseudo partial ordering of ranked pairs that is appropriate for a selected machine learning algorithm, wherein the pseudo partial ordering of ranked pairs is provided to the selected machine learning algorithm, and wherein executing the selected machine learning algorithm, using the ranked pairs, trains a molecular properties model configured to generate a prediction regarding additional molecules supplied to the model.

Another embodiment provides a method for training a molecular properties model that generally includes, selecting at least two molecules to include in a ranked ordering of molecules, wherein the ranked ordering of molecules orders each molecule in the ranked ordering, relative to one another and relative to a property of interest, providing the ranked ordering to a selected machine learning algorithm, and executing the machine learning algorithm to generate a trained molecular properties model.

Another embodiment provides a computer-readable medium containing an executable component that, when executed by a processor, performs operations that generally include receiving, in a computer readable form, a set of property measurements for a plurality of molecules, wherein each measurement provides a value for a property of interest relative to a single molecule, selecting pairs of molecules, from the plurality, wherein a first and second molecule, in a pair of molecules, are ordered relative to one another and the property of interest, and combining the selected pairs of molecules to form the pseudo-partial ordering of ranked pairs.

Another embodiment provides a computer-readable medium containing an executable component that, when executed by a processor, performs operations that generally include, selecting at least two molecules to include in a ranked ordering of molecules, wherein the ranked ordering of molecules orders each molecule in the ranked ordering, relative to one another and relative to a property of interest. The operations generally further include providing the ranked ordering to a selected machine learning algorithm, and executing the machine learning algorithm to generate a trained molecular properties model.

Another embodiment provides a method for evaluating a prediction about a molecule, generated using a computer-implemented molecular properties model. The method generally includes receiving the prediction for at least a test molecule generated by the molecular properties model, wherein the molecular properties model is trained using a set of training data, and wherein the training data comprises a pseudo-partial ordering of molecules. In one embodiment, the molecular properties model may be trained by (i) obtaining a set of property measurements for a plurality of molecules, wherein each measurement provides a value for a property of interest relative to a single molecule, (ii) selecting at least two molecules to include in the pseudo partial ordering, wherein the pseudo partial ordering of molecules orders each therein, relative to one another and relative to a property of interest, and (iii) providing the pseudo partial ordering to a selected machine learning algorithm, wherein the selected machine learning algorithm executed using the training data generates the molecular properties model. The method generally further includes determining the accuracy of the prediction for the test molecule by performing experimentation.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments illustrated by the appended drawings. These drawings, however, illustrate typical embodiments of the invention and are not meant to be limiting of its scope, for the invention may admit to other equally effective embodiments.

DETAILED DESCRIPTION

Embodiments of the invention provide novel techniques for modeling molecular properties. Specifically, embodiments of the invention provide novel techniques for training molecular properties models that order sets of molecules relative to a property of interest. Embodiments of the invention generally train a molecular properties model in one of four ways:

(i) Embodiments of the invention provide novel techniques for generating ranked training data used to train a molecular properties model. Particular embodiments of the invention may be used to generate ranked data from data that is not provided in a ranked form.

(ii) Embodiments of the invention provide techniques that train a molecular properties model using training examples based on ranked data. Embodiments of the invention generate training examples based on ranked data that may be used by a learning algorithm that is not configured to process ranked data.

(iii) Embodiments of the invention provide novel techniques for training molecular properties models that order sets of molecules relative to a property of interest. Particular embodiments of the invention may be used to train a molecular properties model using training data that is not provided in a ranked form, without explicitly generating data in a ranked form. Particular embodiments of the invention may be used to train a molecular properties model by (approximately) minimizing a function of the order assigned to a set of molecules.

(iv) Embodiments of the invention provide novel techniques for training molecular properties models that achieve trade-offs between false negatives and false positives despite not knowing the ideal trade-off apriori.

Although the subsequent discussion describes the invention in terms of rank ordering multiple molecules with respect to a property of interest, the invention is not limited to these kinds of molecular properties. For example, embodiments of the invention may train a molecular properties model to rank order different 3-dimensional conformations of a single molecule. Further, embodiments of the invention may train a molecular properties model to rank order different atoms or bonds in a given molecule with respect to a property of interest (e.g. the pKa or partial charge of a selected atom or bond). Those skilled in the art will observe how the following discussion may be applied in these cases.

An Exemplary Computing Environment

Figure 1:
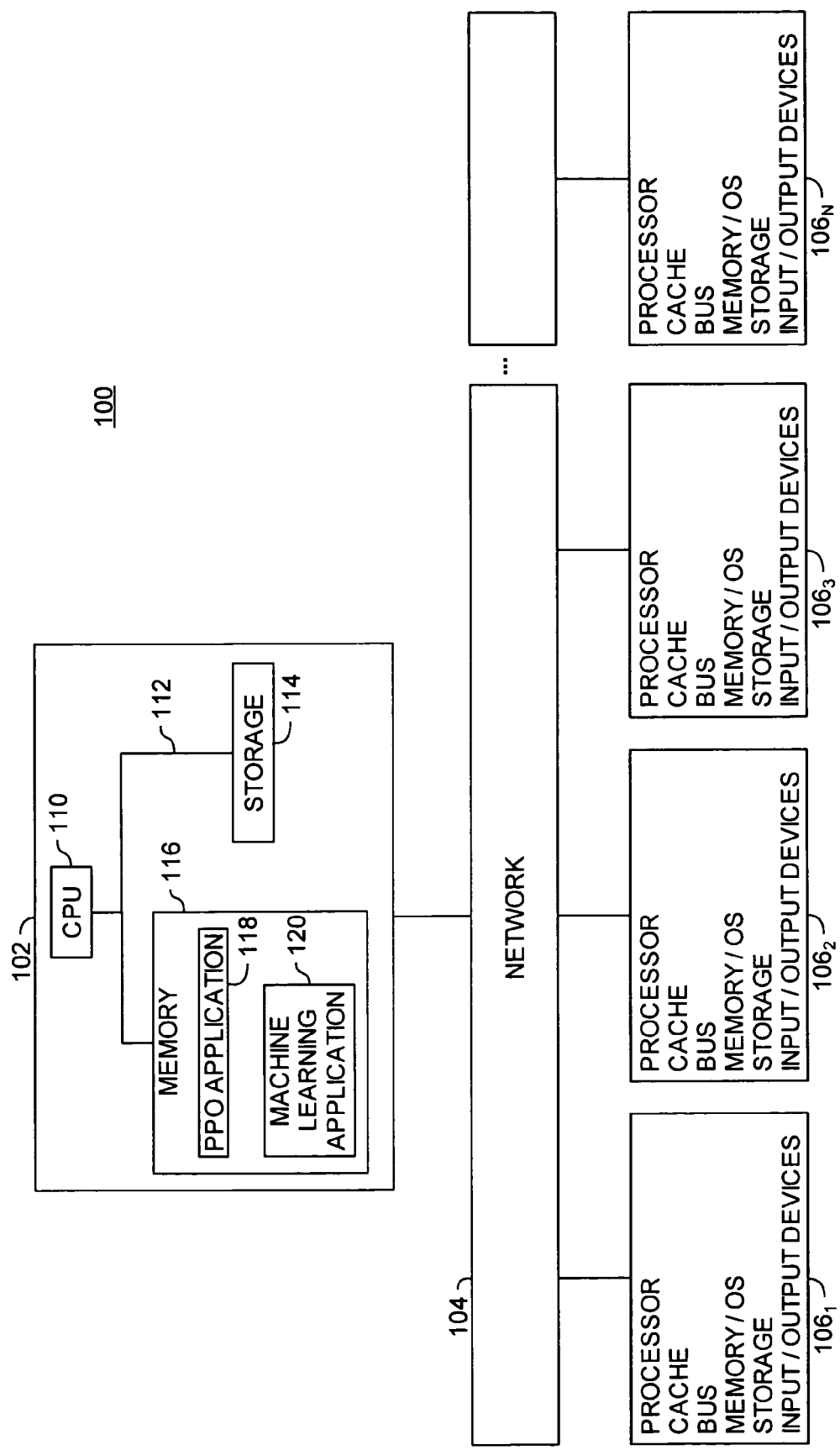
FIG. 1 illustrates a view of a computing environment used to construct a molecular properties model, according to one embodiment of the invention.

Embodiments of the invention may be implemented as computer software products for use with computer systems like the one illustrated in FIG. 1. Such programs may be contained on a variety of signal-bearing media. Examples of signal-bearing media include (i) information permanently stored on non-writable storage media (e.g., a CD or DVD disk); (ii) alterable information stored on writable storage media (e.g., floppy disks within a diskette drive or hard-disk drive); and (iii) information conveyed to a computer by a communications network, including wireless communications. The latter embodiment specifically includes information made available on the Internet and other networks. Such signal-bearing media, when carrying computer-readable instructions that implement the methods of the invention, represent embodiments of the invention.

FIG. 1 illustrates an exemplary computing environment 100. Network 104 connects computer system 102 and computer systems, $106_{1-N}$. In one embodiment, computer 102 comprises a server computer system configured to respond to the requests of systems $106_{1-N}$ acting as clients. Illustratively, computer systems 102 generally include a central processing unit (CPU) 110 connected via a bus 112 to memory 116, storage 114, and network interface 104, and the like. Computer systems 102 and $106_{1-N}$ also typically include input/output devices such as a mouse, keyboard, and monitor, and may include other specialized hardware Memory 116 includes machine learning application 120 and PPO application 118.

Embodiments of the invention may be implemented using any available computer system and adaptations are contemplated for both known and later developed computing platforms and hardware. Accordingly, the methods described below may be carried out by software applications configured to execute on computer systems ranging from single-user workstations, client server networks, large distributed systems employing peer-to-peer techniques, or clustered grid systems. In one embodiment, computer system 102 and computer systems $106_{1-N}$ may be connected to form a high-speed computing cluster such as a Beowulf cluster, or other clustered configuration. Those skilled in the art will recognize that a Beowulf cluster is a method for creating a high-performance computing environment by connecting inexpensive personal computer systems over high-speed network paths. In such an embodiment, computer system 102 may comprise a master computer used to control and direct the scheduling and processing activity of computer systems $106_{1-N}$.

Further, the computer systems used to practice the methods of the present invention may be geographically dispersed across local or national boundaries using network 104. Moreover, predictions generated for a test molecule at one location may be transported to other locations using well known data storage and transmission techniques, and predictions may be verified experimentally at the other locations. For example, a computer system may be located in one country and configured to generate predictions about the property of interest for a selected group of molecules, this data may then be transported (or transmitted) to another location, or even another country, where it may be the subject of further investigation e.g., laboratory confirmation of the prediction or further computer-based simulations.

Creating Ranked Training Data

Rather than use training examples that provide a measurement for a selected property of interest relative to a single molecule, embodiments of the invention use training examples based on a relative measurement between two or more molecules. The term "ranked data" refers to sets of molecules wherein the measurement for the property of interest for one molecule is deemed to be greater (or lesser) than the activity of the other molecules in the set. For example consider the set of two molecules {A, B}, if molecule A has a reported measurement value of 85, and molecule B has a reported measurement value of 70, then molecule A is said to be ranked greater than molecule B. This is represented herein by the inequality (A>B), or, for short, just the ranked pair: (A, B). Although described herein using ranked pairs of molecules, those skilled in the art will readily recognize that the techniques disclosed herein may readily be extended to a vector ranking that includes an arbitrary number of molecules, ranked relative to one another (e.g., the ranking vector <a, b, c, d> wherein the ranking of one molecule is greater than its right neighbor, and lower then its left neighbor, where one exists).

For example, data taken from Table 1 of the Journal of Medicinal Chemistry, volume 48, pages 3118-3121, shows that compound 2a binds to Chk1 kinase with an affinity of 3 nanomolar, whereas compound 2c binds with an affinity of 10 nanomolar. Thus, the ranked pair (2a, 2c) may be used to represent a ranking of compounds 2a and 2c relative to this property of interest.

As noted above, embodiments of the invention may be used to model molecular properties that correspond to properties of atoms or bonds of a single molecule, or to alternative representations or conformations of a molecule. For example, embodiments of the invention may be used to model an ordering of the possible three dimensional conformations of a molecule. Here conformation A for a molecule is ranked higher than conformation B if conformation A is more likely in some environment (e.g. a particular solvent). Thus, similar to embodiments used to process ordered pairs of molecules it may likewise consider ordered pairs of three dimensional conformations of a given molecule.

In addition, property measurements may be related to atoms or bonds in a molecule. For example, the invention may be applied to construct a model of the pKa of each atom in a molecule; in this case the model will rank the atoms according to their pKa. Thus, the ranked pair (A, B) may represent a ranking of different atoms of a single molecule, relative to their pKa.

Using property measurements available for a set of molecules, a "pseudo-partial order" ("PPO") is constructed. A pseudo-partial order of molecules is constructed from individual pairs of molecules, according to the available measurements and selection criteria. A partial order (represented using the symbol "≦") is defined mathematically as a relation on a set with the properties of reflexivity i.e., antisymmetry i.e. (A≦B),(B≦A)⇒A=B and transitivity i.e. (A≦B), (B≦C)⇒(A≦C). A "pseudo-partial order" ("PPO") is defined herein as the relation on a set that can be viewed as a partial order for which antisymmetry does not hold and for which transitivity is does not hold. A PPO can be viewed as a partial order that has been corrupted by noise, or had errors introduced.

A PPO is partial because not all possible ranked pairs from the set of molecules are necessarily included. For example, consider molecules A, B, and C. If a PPO of these three molecules (relative to a property of interest) includes the following two ranked pairs: (A, B), and (A, C); it remains unknown whether the correct full ordering is (A, B, C), or (A, C, B).

Anti-symmetry does not hold for a PPO as the pairs (A, B) and (B, A) may both be contained in the PPO because one of the relationships is inferred from noisy or misleading data. Transitivity does not necessarily hold for a PPO as inconsistencies in experimental results may not imply transitivity for a given molecular property.

Accordingly, as used herein, a "pseudo-partial order" (or PPO) includes a set of ranked pairs. For example, the above set {(A, B), (A, C)} is an example of a PPO. The ranked pairs included in a PPO may be inconsistent and include both (A, B) and (B, A) as ranked pairs. Further, a PPO may include the same ranked pair more than once, and may not be transitive across ranked pairs. A PPO may be considered as a partial order corrupted by noise. Noise-tolerant learning algorithms may then induce a model that assigns a partial order to a set of molecules.

The elements of a PPO may be associated with weights to create a weighted PPO. The meaning of these weights can vary, but one interpretation is that the weights correspond to a measure of the confidence in the correctness of the given element i.e. the pair (A,B) may be assigned the weight 1.2, while the pair (B,A) may be assigned the weight 4.5, the interpretation being that the pair (B,A) is more likely to be the correct ordering of the two molecules included in the pair.

Those skilled in the art will recognize that PPOs may be represented in many ways. For example a PPO may be represented as a set of ordered tuples (A,B,C,D) wherein molecules in the ordered tuple are considered to be ranked higher (or lower) than molecules that succeed them in the ordered tuple. This set of ordered tuples can contain inconsistent tuples wherein one molecule e.g. A is ranked both higher and lower than another molecule e.g. B.

Those skilled in the art will further recognize that PPOs may be represented using permutations of molecules, or sets of permutations of molecules. Further, when represented using sets of permutations of molecules, the permutations in the set may be assigned weights such that a weighted PPO is represented as a probability distribution over permutations of the molecules. Those skilled in the art will further recognize that the set of all permutations forms the symmetric group. They will further recognize that cosets of the symmetric group represent sets of partially constrained permutations of the molecules i.e. the rank order of some molecules is specified; however, it is not specified for all sets of molecules. Those skilled in the art will recognize, therefore, that PPOs may be represented as cosets of the symmetric group and probability distributions over the cosets of the symmetric group (see "Cranking: Combining Rankings Using Conditional Probability Models on Permutations", Lebanon and Lafferty, Advances in Neural Information Processing Systems 15 incorporated herein in its entirety). Those skilled in the art will further recognize that a PPO may be represented as a cross product between a pair of sets. Given two sets {A,B, C,D} and {E,F,G}, the cross product consists of all pairs where the first element is chosen from the first set and the second element is chosen from the second set. Furthermore, a PPO may be represented as a set of such cross products. Although the discussion below is written in terms of PPOs, and in particular it is written in terms of PPOs represented as pairs of molecules, those skilled in the art will recognize that alternative representations, including those just described, are envisioned and are thus encompassed by the invention.

Further, this description refers to embodiments of the invention. The invention, however, is not limited to any specifically described embodiments; rather, any combination of the described features, whether related to a described embodiment, implements the invention. Further, although various embodiments of the invention may provide advantages over the prior art, whether a given embodiment achieves a particular advantage, does not limit the invention. Thus, the features, embodiments, and advantages described herein are illustrative and should not be considered elements or limitations, except those explicitly recited in a claim. Similarly, references to "the invention" should neither be construed as a generalization of the inventive subject matter disclosed herein nor considered an element or limitation of the invention.

Creating a Pseudo-Partial Ordering (PPO) from Reported Measurements (a) Continuous Measurements of a Property of Interest In one embodiment, available measurements for the property of interest are used to create a PPO that includes a plurality of ranked pairs. Each pair includes two molecules, wherein one molecule has a greater measured value for the property of interest than the other molecule in the pair, e.g., the pair (A, B). Individual ranked pairs that satisfy any provided selection criteria are then included in a PPO. The ranked pairs of the PPO may then be used as training examples to train a molecular properties model. Continuous measurements of the property of interest, relative to individual molecules, are used to select pairs of molecules to include in a PPO. The measurements may be based on the results of direct experimentation, obtained from scientific literature, or on the results of in-silico calculations generated using a software application configured to simulate chemical activity and reactions.

Similarly, a ranked pair may be constructed using different measurements for different substituent parts of a single molecule e.g. atoms or bonds in the molecule or different representations of a molecule e.g. alternative three dimensional conformations of the molecule.

Figure 2:
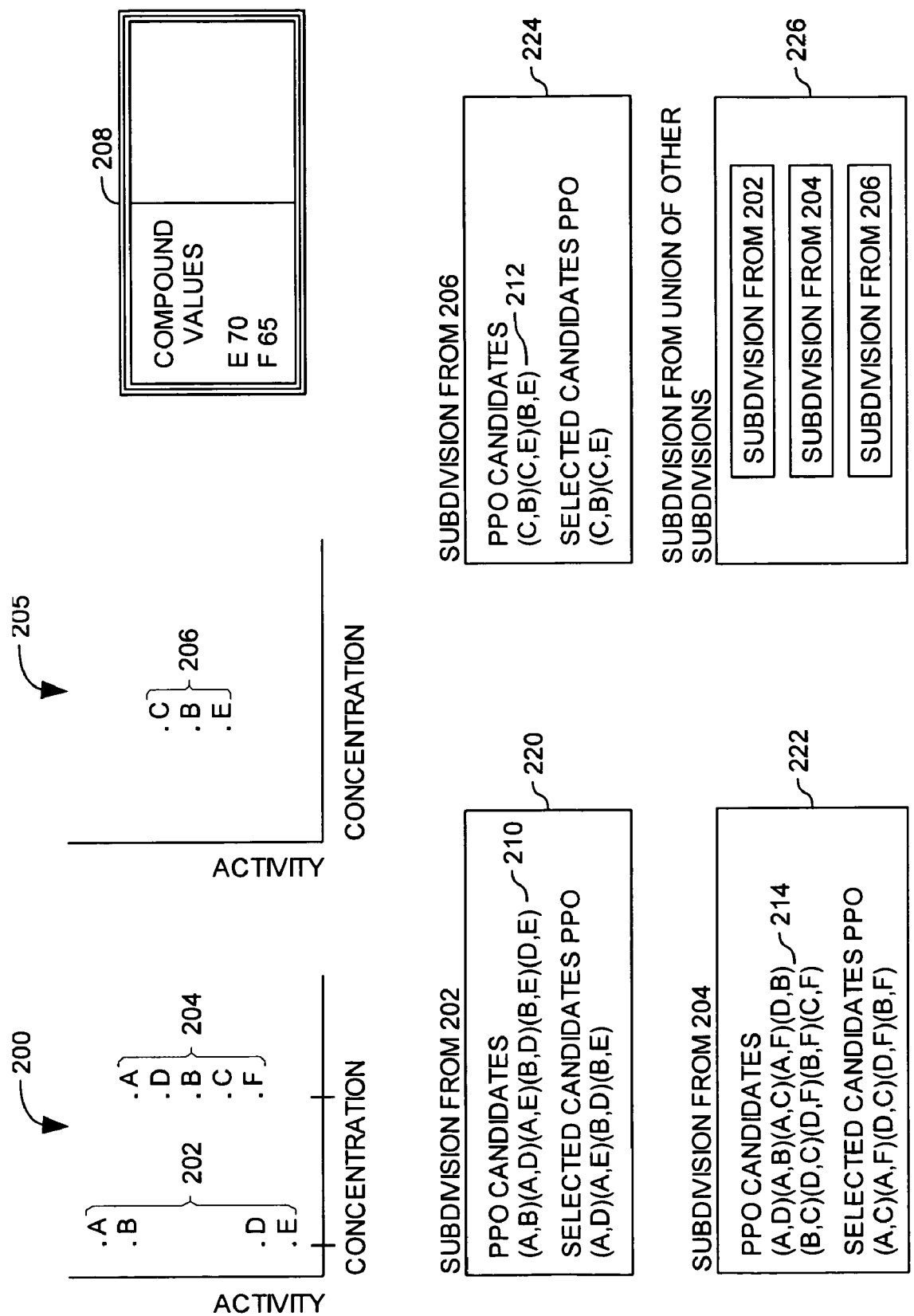
FIG. 2 illustrates exemplary measurements of a property of interest reported for a set of molecules that may be used to construct a pseudo-partial ordering, according to one embodiment of the invention.

FIG. 2 illustrates reported measurements of molecule activity that may be used to construct a PPO, according to one embodiment of the invention. In this example, individual molecules are represented using the capital letters A-F. Illustratively, graph 200 includes two sets of measurements, 202 and 204, and graph 205 includes one set of measurements 206. The measurements of molecule activity are plotted against the y axis of the graphs 200 and 205. Set 202 includes a reported measurement for molecules A, B, D, and E. Set 204 includes a reported measurement for molecules A, B, C, D, and F, at a different concentration level from set 202 (as plotted on the x axis). Set 205 includes measurements reported for molecules C, B, and E. In addition set 208 includes activity measurements for molecules E and F reported in scientific literature (e.g., a peer-reviewed journal).

The measurements for an individual molecule plotted in graphs 200 and 205 fluctuate. For example, the measurement for molecule B is different in sets 202, 204 and 206. When comparing data obtained from actual laboratories, this state is common as different labs may employ different protocols or different quality standards. Also, the experiments themselves may be carried out under substantially different conditions. Thus, the reported value for an individual molecule may be different, depending on the source of the measurement data. Further, when using measurements obtained in-silico (e.g., using a computer simulation), the measurements may also be inconsistent with those obtained in the laboratory e.g. the measurements may be obtained with respect to arbitrary units or may be consistently biased higher or lower than reality.

The relative ordering of the molecules illustrated in graphs 200 and 205, however, is fairly consistent, regardless of the source. This also commonly occurs when comparing actual data for the same set of molecules. Illustratively, molecule A is reported as more active than any other molecule in each of the sets 202 and 204. The PPO of ranked pairs captures the relative nature of these measurements by representing molecule activity as ranked data.

In one embodiment, the molecules that have reported measurements for the property of interest are used to generate a set of candidate pairs. FIG. 2 illustrates the molecules A, B, C, D, E, and F, divided into subdivisions 220, 222 and 224. The subdivision 220 includes candidate pairs 210 taken from set 202. Similarly, subdivisions 222 and 224 include PPO candidate pairs 212 and 224 taken from sets 204 and 206, respectively.

Candidate pairs are assigned to subdivisions based on attributes of the property data. For example, all molecules tested under identical conditions could constitute a subdivision. As another example, all molecules tested against human enzyme could constitute a subdivision or all molecules for which Ki data are available might constitute a subdivision. Also, molecules may belong to several subdivisions. For example, subdivision 226 includes PPO candidate pairs from the union of the sets 202, 204 and 206.

For each subdivision, a set of criteria is used to select molecules to include in a ranked pair. The criteria used to determine a ranking between two molecules from the same subdivision may include, without limitation, the relative magnitude of the measurement being above some threshold, the absolute difference in magnitude of the reported measurement being above some threshold, and the probability that the measured values fall outside any experimental error intervals between two molecules. For example, it may be known (or believed) that laboratory 1 has lower measurement uncertainty than laboratory 2, thus the criteria for laboratory 2 will be more stringent. The appropriate criteria are determined by considering any appropriate factors including: the reported measurement uncertainty of an experiment, the reported measurement uncertainty of related experiments, measurement differences across species, measurement differences across laboratories, estimates for the error inherent in experimental data, uncertainty measurements regarding simulations carried out using computer software, and estimates or beliefs about any of these.

Whenever two molecules, e.g., molecule A and molecule B from set 202, belong to the same sub-division, and also satisfy the appropriate criteria to be assigned a ranking (i.e., (A, B) or (B, A)) the ordered pair is added to a PPO. A pseudo-partial ordering is constructed by combining all the ordered pairs that satisfy the criteria from each sub-division of molecules.

From the set of molecules 202, the candidate pairs 210 include all possible molecule rankings based on the reported values. Depending on the selection criteria, however, not all possible pairs will be included in the PPO. Illustratively, the close values of the reported measurements of molecules (A, B) and (D, E) from set 202 may exclude these two pairs from the PPO. The ranked pairs (A, D), (A, E), (B, D), and (B, E), however, may satisfy the selection criteria and are included in the pseudo partial ordering. Similarly, subdivision 222 and 224 include candidate pairs 212 and 214. Note, one of the included ranked pairs, (C, B), from subdivision 224 ranks the same two molecules differently than a ranked pair (B, C) from set 202. Because measurements for the property of interest may be obtained from different sources, different results may occur. Depending on the criteria used to select candidates from each subdivision, either or both of these ordered pairs may be included in a PPO. Additional ranked pairs may be derived from literature values (e.g., the ranked pair (E, F)) from set 208.

Those skilled in the art will recognize that the measurements, orderings, candidate sets and PPOs illustrated in FIG.

2 are exemplary, and not meant to reflect the activity measurements for molecules that would be obtained using reported, estimated, or simulated values for actual molecules.

As discussed previously, the embodiments of the invention may be used to model molecular properties of individual atoms or bonds in a molecule, or of alternative representations of a molecule. In these cases the subdivisions used for training data will typically consist of all of the atoms, bonds or representations of a given molecule.

(b) Discrete Measurements of a Property of Interest

In one embodiment, a PPO of ranked pairs may be constructed from reported measurements that assign individual molecules with a discrete label for the property of interest. For example, a molecule may be labeled as "active" or "inactive" for a given property of interest, or "positive" or "negative" for the property. Generally, a molecule labeled as "active" or "positive" may be paired with those labeled "inactive" or "negative" to form a ranked pair. The measurements for an individual molecule may be obtained from any of the sources described above regarding continuous measurements of molecule activity.

Similarly, a ranked pair may be constructed using different measurements for different substituent parts or representations of a single molecule when one substituent is labeled "positive" and another substituent is labeled "negative" for a given property of interest e.g. the lability of bonds may be analyzed where labile bonds may be labeled "positive" for lability and non-labile bonds may be labeled "negative".

Figure 3:
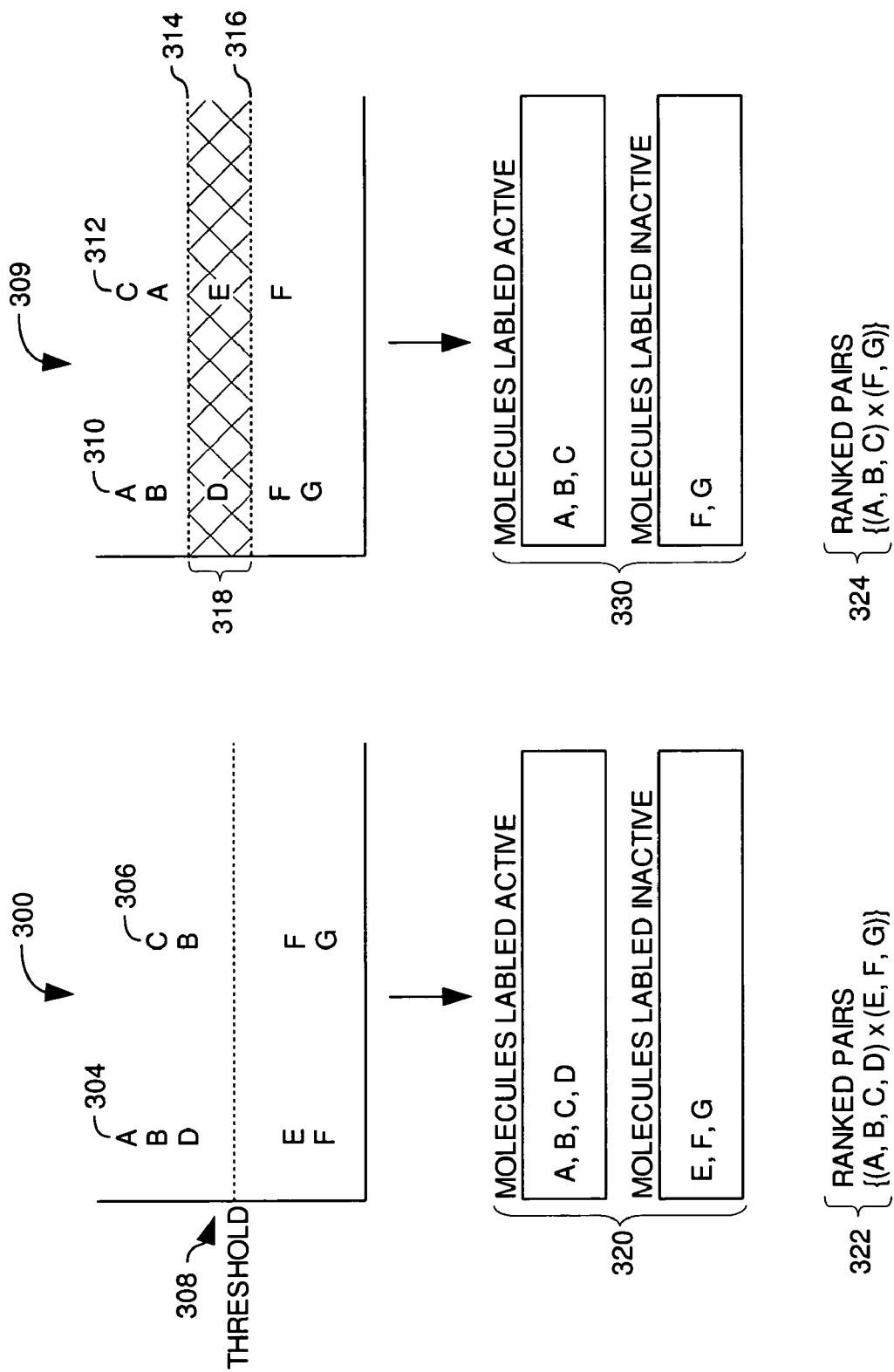
FIG. 3 illustrates multiple sets of molecules and assigned activity values that may be used to construct a pseudo-partial ordering, according to one embodiment of the invention.

Often, the label assigned to an individual molecule is based on whether the measurement of a property of interest is above or below an arbitrarily selected threshold. For example, from data taken from Table 1 of the Journal of Medicinal Chemistry, volume 48, pages 3114-3117, one could choose an arbitrary cutoff of 10 micromolar and label molecules that bind to the TRalpha receptor as "positive" if their binding affinity is less or equal to 10 micromolar, and "negative" otherwise. In this case, compounds 4b, 2a, 3, 9e-k would be labeled "positive" and compounds 9a-d "negative". FIG. 3 illustrates graphs 300 and 309 plotting reported measurements for four sets of molecules (sets 304, 306, 310, and 312). In this example, individual molecules are represented using the capital letters A-G. Graph 300 includes two sets of measurements, 304 and 306, and graph 309 includes sets 310 and 312. The measurements of molecule activity are plotted against the y axis of the graphs 300 and 309.

Illustratively, graph 300 includes threshold 308 separating the molecules in sets 304 and 306 into two groups. Molecules above the threshold are labeled "positive" for the property of interest, and molecules below the threshold are labeled "negative." Box 320 illustrates molecules from graph 300 sorted based on whether the measurement for a given molecule is above or below the threshold 308. From these sorted molecules, a PPO of ranked pairs may be generated by selecting each possible combination of a molecule selected from those labeled "active" paired with a molecule from those labeled "negative." Note that this corresponds to the cross-product representation for PPOs discussed above and illustrated in 322. Additionally, ranked pairs constructed in this manner may also be filtered using any appropriate selection criteria.

Similarly, a PPO may be constructed using the molecules plotted in graph 309. The threshold 318 illustrated in graph 309, however, includes an upper bound 314 and a lower bound 316. This separation creates a region (illustrated using cross hatching) for which no assertion is made regarding the property of interest. That is, molecules above the upper bound 314 are considered to be ranked above the molecules below the lower band 316. Molecules in the bounded region are not labeled either way, or used to construct a ranked pair. From these partitions, ranked pairs are constructed by combining molecules above the threshold with molecules from below the threshold 318 as illustrated in 330. Using the upper and lower bounds (314 and 316) allows more stringent criteria to be applied in selecting ranked pairs to include in PPO 324.

As described above, the ranked pairs included in a PPO may be constructed using both continuous and discrete measurements of a property of interest. Additionally, ranked pairs may be created from measurements that directly report relative measurements of a property of interest for two (or more) molecules. For example, some experimental protocols may determine the relative activity of two molecules against a target. Thus, if a measurement directly provides a ranking of two molecules relative to a property of interest, then the two molecules may be used to construct a ranked pair included in a PPO.

Virtual Molecules and Virtual Data

Optionally, ranked pairs may be generated using molecules for which a measurement of the property of interest is unavailable for one molecule included in the ranked pair. For example, the binding affinity of a randomly selected molecule against a protein receptor is likely to be very low. Accordingly, a ranked pair may be created from such a molecule and one known to have strong affinity for the protein receptor. Such a ranking may be part of a PPO based on relative data measurements, or on a label indicating the molecule is above or below a given threshold. A measurement for the property of interest is assumed to be very low or "negative" relative to a molecule known to have a high level of activity, or labeled "positive." Detailed examples of using assumed values for some activity measurements are described in a commonly owned co-pending U.S. patent application Ser. No. 11/074, 587 named above entitled "Methods for Molecular Property Modeling Using Virtual Data."

Also, the molecules selected to include in a ranked pair may be generated using computational simulation techniques. Methods for enumerating a set of synthesizable molecules are described in a commonly owned U.S. patent, U.S. Pat. No. 6,571,226, entitled "Method and Apparatus for Automated Design of Chemical Synthesis Routes," incorporated by reference herein in its entirety, alternative methods are possible and fall within the scope of this invention. The property data, for such virtual molecules may be generated based on reasonable assumptions, like those regarding assumed virtual training data described in the Ser. No. 11/074,587 application or from software or hardware applications configured to simulate activity experiments to obtain a measurement value. Illustrative embodiments of hardware and software configured to process molecular properties data are disclosed in commonly assigned U.S. patent application Ser. No. 10/449,948, "Method and Apparatus For Quantum Mechanical Analysis of Molecular Systems," and U.S. patent application Ser. No. 10/452,481 Method and Apparatus for Molecular Mechanics Analysis of Molecular Systems."

A PPO of ranked pairs may then be constructed using the virtual molecules and/or virtual data using the techniques described above. It is often the case that in silico simulations of molecular properties are far more effective at producing rank orderings of molecules than they are at predicting actual property values. In this case the output may be used to directly construct a PPO.

Weighting Data

In one embodiment weights may be assigned to the ranked pairs included in a PPO. The value is assigned to reflect a measure of confidence in the accuracy of a ranked pair. That is, the weighted value reflects an estimate of confidence in the validity of the assertion that molecule A is ranked greater than molecule B relative to the property of interest for the ranked pair, (A, B).

Additionally, molecules may be weighted to normalize the impact on the learning process that can occur when one molecule appears over and over again in the ranked pairs of a PPO. For example, a molecule with a high activity value may appear in a disproportionate number of ranked pairs in a PPO. Multiple appearances of a molecule may bias the model constructed with such a PPO by exaggerating the importance of the frequently occurring molecule. Another way in which a molecule may appear a disproportionate number of times is in articles in the scientific literature. These articles commonly compare the activity of novel molecules against a common reference molecule. In this case there will be a large number of reported data points for the reference molecule. Once the completed training set is used to train a molecular properties model, if the model "sees" the one molecule over and over again as a learning example, it may simply learn to predict whether an arbitrary molecule is, in fact, the same as the one seen over and over.

Decreasing the weight assigned to each instance of a ranked pair for such a dominant molecule helps prevent this problem. For example, if the dominant molecule appears 10 times more frequently than others, each instance of a ranked pair with the dominant molecule may be weighted to contribute a $1/10^{th}$ weight. Note however, this weighting is not a reduction of confidence in the ranking of the dominant molecule; rather it normalizes the contribution made by the dominant molecule.

Persons skilled in the art will recognize that embodiments of the invention may use other techniques for assigning a weighted value to the ranked pairs of a PPO. Accordingly, the weighting methods described above are included for illustrative purposes, and should not be construed to limit the scope of the invention.

Figure 4A:
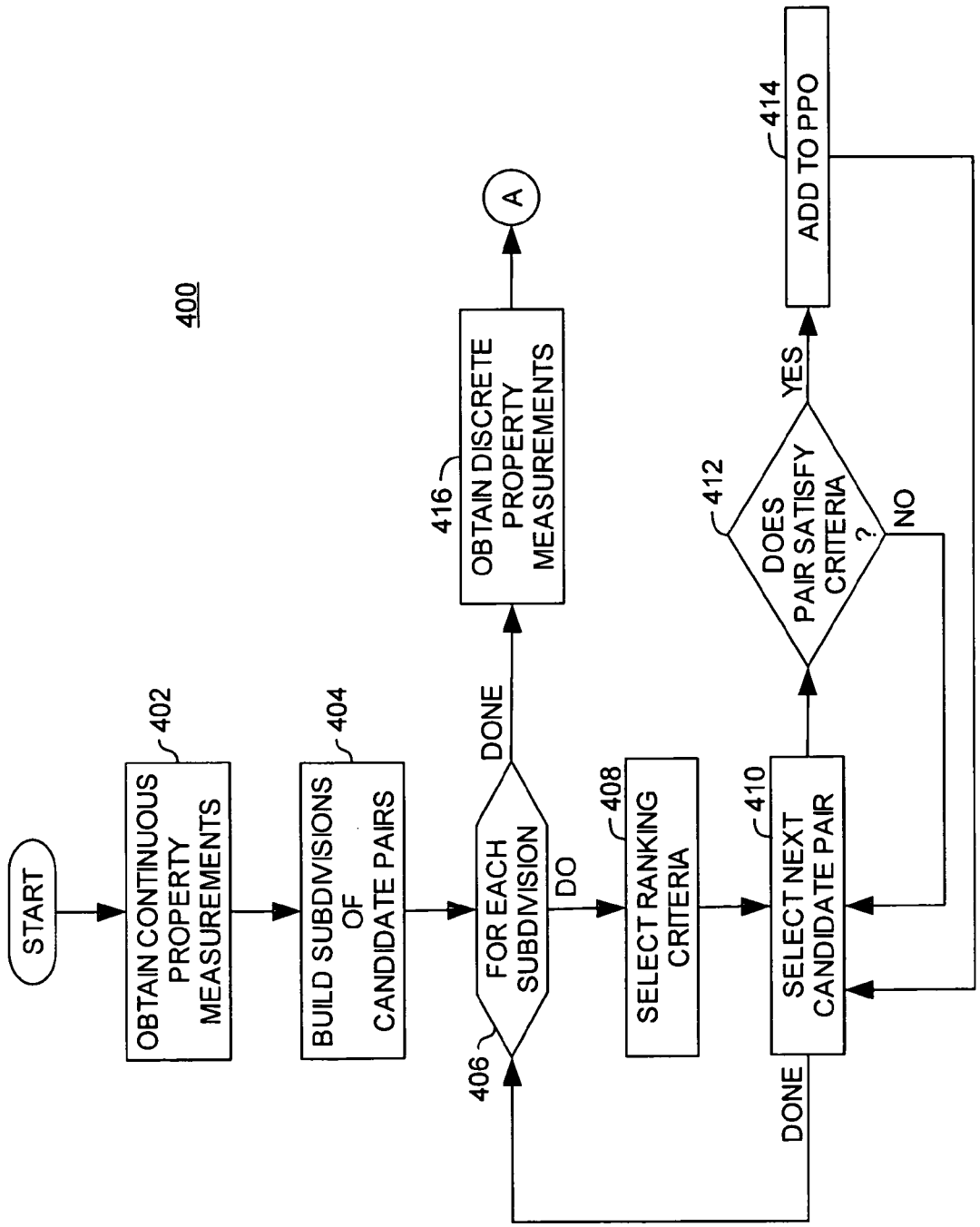
FIG. 4 illustrates a method for constructing a pseudo-partial ordering from a set of molecules, according to one embodiment of the invention.
Figure 4B:
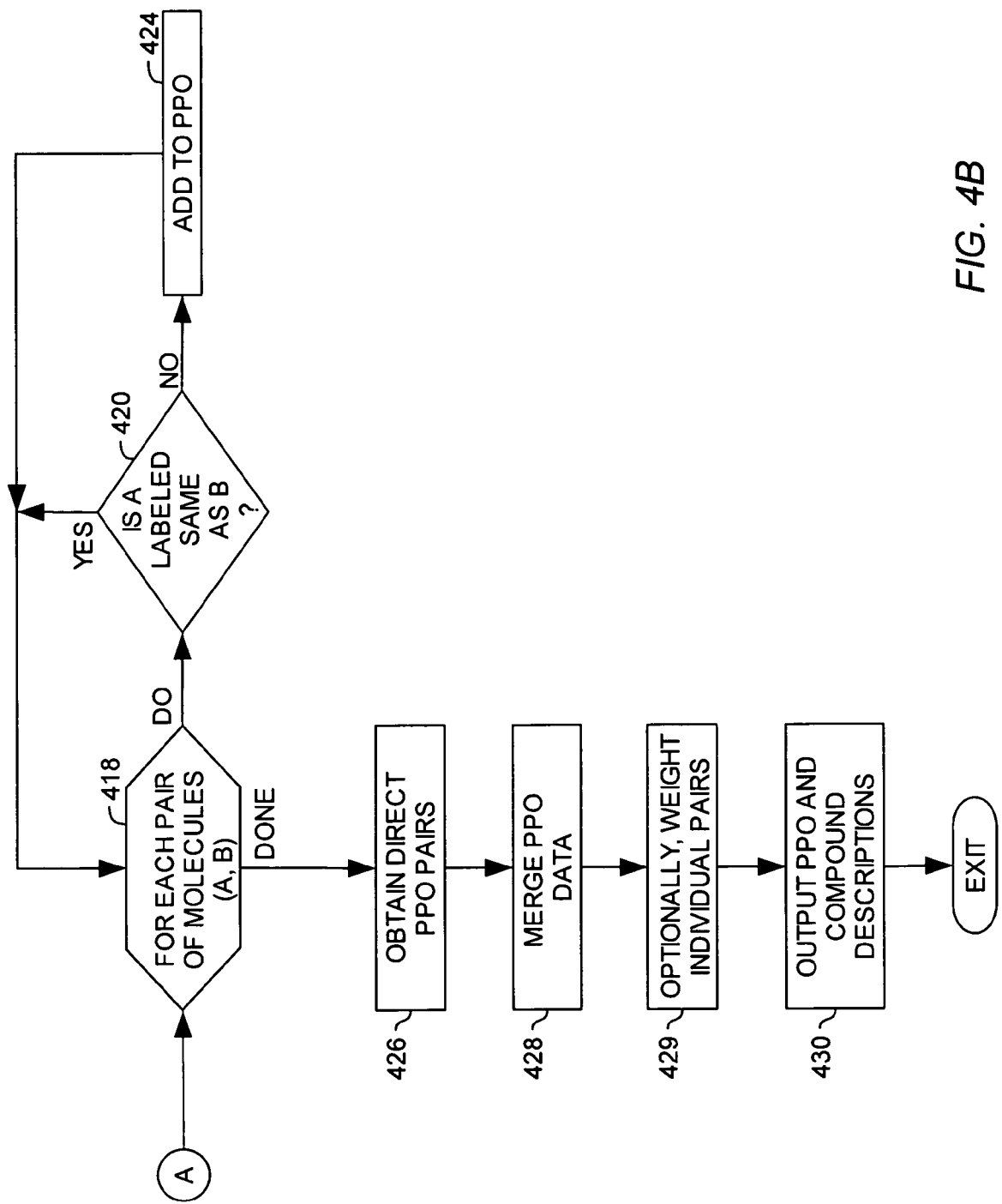

FIG. 4 illustrates a method 400 for generating a PPO, according to one embodiment of the invention. The method 400 begins at step 402 where measurement values reported for a set of molecules are obtained. The measurement values assign a "score" to each molecule, relative to the property of interest. At step 404, the molecules are divided into subdivisions of candidate ranked pairs (e.g., the subdivisions of candidate rankings 220 and 222 illustrated in FIG. 2).

At step 406, a loop comprising steps 408-414 is performed for each subdivision generated at step 404. At step 408, ranking criteria used to select ranked pairs from the candidates of the current subdivision are selected. At step 410, each candidate pair in a given subdivision is processed to determine whether to include the candidate pair in the PPO. If the current candidate pair satisfies the selection criteria, then it is added to the PPO (step 414) and the next candidate pair is processed. Otherwise, the next candidate pair is processed. Steps 410-414 repeat for each candidate pair in the current subdivision. Once all subdivisions of molecules have been processed according to steps 406-414, the method 400 proceeds to step 416.

At step 416, molecule activity data that assigns a label indicating presence or absence of a property of interest to each of a set of molecules is obtained. For example, each molecule may be labeled with an indication of "positive" or "negative." At step 418, a loop comprising steps 418-424 tests pairs of molecules selected from those labeled at step 416. Each candidate pair is evaluated (step 420). The evaluation of step 420 determines if the labels for the two molecules in a candidate pair indicate that one molecule is ranked above the other. If not, then the candidate pair is not added to the PPO. Otherwise, the candidate pair is added to the PPO. After evaluating the candidate pairs, the method 400 proceeds to step 426. At step 426, data that directly provides a ranked ordering of two molecules relative to the property of interest is included in the PPO.

At step 428, the ranked pairs added to the PPO at steps 414, 424 and 426 are merged, and the resulting PPO is output at step 430. Those skilled in the art will recognize that in a particular embodiment, not all types of molecule data, as represented by steps 402, 416 and 426 are required to construct a PPO of ranked pairs. For example, in one embodiment, only data assigning a label of "positive" or "negative" to individual molecules is used to construct the PPO. In another, only reported measurements are used. In still another embodiment, a PPO may be generated from ranked pairs generated from virtual data and virtual molecules. The actual selection will depend on, among other factors, the availability, cost, and reliability of data regarding the property of interest, and available computing power. Optionally, at step 429, the ranked pairs selected to be included in the PPO may be weighted. For example, the ranked pairs may be weighted to normalize the impact of a molecule that occurs in multiple ranked pairs of the PPO.

While the foregoing was discussed in the context of molecular properties of a molecule as a whole, the invention equally may be applied to parts of a molecule e.g. atoms or bonds, or to alternative representations of a molecule e.g. three dimensional conformations.

Training a Molecular Properties Model using Ranked Data

As described above, embodiments of the invention may use several different techniques for selecting the ranked pairs to include in a PPO. Once the PPO is selected, the ranked pairs included in the PPO may be used as training examples to train a molecular properties model. Both novel machine learning algorithms, as well as general or specific machine learning algorithms may use the ranked pairs included in the PPO as training examples. In one embodiment, the molecular properties model includes a software application configured to execute a machine learning algorithm, using the ranked pairs of the PPO as training examples. Additionally, embodiments of the invention provide methods for using non-ranking algorithms (e.g., a classification or concept learning algorithm) trained using a modified form of the ranked pairs included in the PPO. Embodiments of the invention may use PPO data represented as permutations, sets of permutations, cross products or sets of cross products as discussed previously. Several illustrative examples of learning algorithms are described below.

Figure 5:
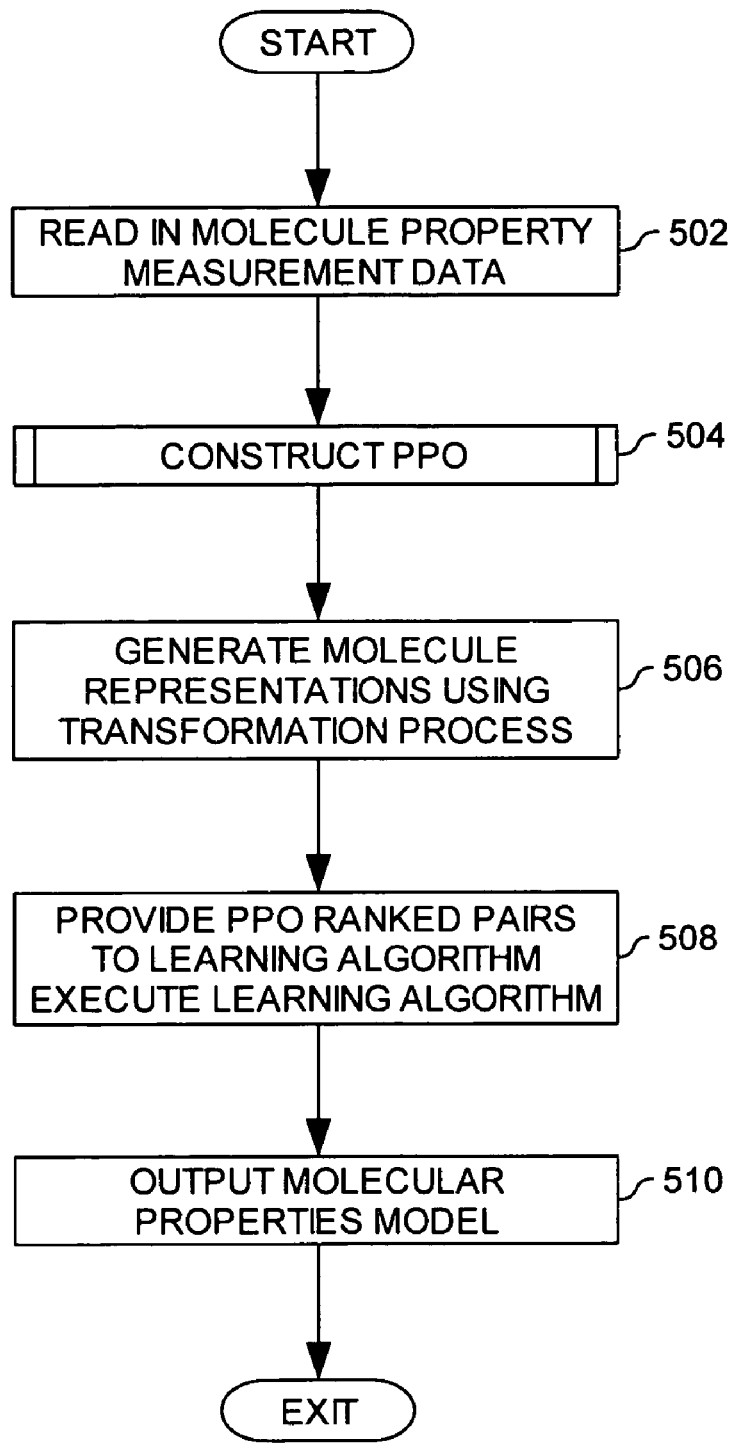
FIG. 5 illustrates a method for training a molecular properties model from a pseudo-partial ordering of ranked pairs, according to one embodiment of the invention.

FIG. 5 illustrates a method 500 for training a molecular properties model from a PPO of ranked pairs, according to one embodiment of the invention. As described above, the PPO includes a set of ranked pairs, wherein each ranked pair orders the two molecules represented by the pair, relative to the property of interest.

The method 500 begins at step 502 by obtaining a set of molecule descriptions together with measurements of the property of interest for each molecule. Data regarding the property of interest may be in any of the forms described above (e.g., continuous measurements of activity or discrete labels), and further, molecules and property data may be obtained from the results of either actual or in-silico experimentation. At step 504, a PPO of the molecules is generated or obtained. One embodiment of a method for creating a PPO is illustrated by the method 400 of FIG. 4.

Once the PPO of ranked pairs is constructed, a transformation process (step 506) is used to create a representation of the molecules in the PPO used to train a molecular properties model. In one embodiment, the transformation process may include a software application configured to receive a representation of the molecules in a ranked pair and generate a representation appropriate for a selected machine learning algorithm. For example, the transformation process may provide a vector representation of the molecules in a ranked pair, or may provide a conformational analysis of the molecules to generate a representation that describes three dimensional conformations of the molecules in the pair. Embodiments of present invention may make use of representations involving 10s to 100s of millions of features such as n-point pharmacophores where n is 3, 4, 5 or larger.

Generally, the molecule descriptions generated by the transformation process at step 506 encode the structure, features and properties that may account for one molecule in a ranked pair having a greater activity than the other molecule. Accordingly, properties such as present functional groups, steric properties, electron density and distribution across a functional group or across the molecule, atoms, bonds, locations of bonds and other chemical or physical properties of the molecule may all be used as part of the representation generated at step 506.

When the present invention is applied to the modeling of molecular properties of atoms or bonds in a molecule the representations maybe be different. For example, a given atom may be represented by a list of all the functional groups in which it is contained, or by a list of all paths through the molecule in which it is contained. Similarly, when the invention is applied to the modeling of alternative representations or conformations of a molecule the representation used by the learning algorithm will contain features that differentiate between different conformations.

At step 508, the molecule descriptions, together with the pseudo partial ordering, are processed by a machine learning algorithm configured to "learn" using training examples that include the ranked pairs of a PPO. At step 510, the resulting molecular properties model is output. The resulting molecular properties model is configured to generate a prediction for representations of molecules supplied to the model. The prediction may be a prediction of a value for the property of interest for a particular molecule, or may be a rank ordering (e.g., a PPO) for a group of molecules supplied to the model. In a particular embodiment, the prediction provides a ranking for a pair of molecules, relative to the property of interest.

The PPO used at step 508 may be represented as a list of pairs, or may be represented as a list or set of permutations or a list or set of cross products. Those skilled in the art will recognize that the PPO used in step 508 may be represented in many different ways. The present invention is not limited to any particular representation.

Illustrative Machine Learning Algorithms

In one embodiment, the pseudo partial ordering of ranked pairs is supplied to a learning algorithm not directly capable of using ranked data at step 510, e.g., a classification learning algorithm. In such an embodiment, the ranked pairs included in the PPO are used as separate data points and modified to include the label +1 if molecule A is ranked above molecule B (e.g., (A>B)) or labeled −1 if molecule B is ranked above molecule A (e.g., (A<B)). The resulting data set is fed to an arbitrary classification learning algorithm. Such an embodiment allows classification algorithms to use ranked data.

In another embodiment, a PPO is constructed and provided to a margin or kernel based learning algorithm at step 510. Each pair of molecules (A, B) is provided to the algorithm as (A-B) (i.e., an appropriate representation of the difference between molecules A and B), and labeled as described above for classification algorithms. Such an embodiment may then generate a linear combination of data points i.e. a model whose value on a new molecule C is a linear combination of the dot products between representations of C and molecules in the training set. This linear combination can be interpreted as a linear combination of molecules and then used to assign a numerical score to arbitrary molecules. The resulting model can be used to assign a total linear ordering (or a partial ordering) to an arbitrary set of molecules.

In another embodiment, the learning algorithm used at step 508 may comprise learning algorithms such as Boosting, a variant of Boosting, Rank Boosting, Alternating Decision Trees, Support Vector Machines, the Perceptron algorithm, Winnow, the Hedge Algorithm, an algorithm constructing a linear combination of features or data points, Decision Trees, Neural Networks, Genetic Algorithms, Genetic Programming, logistic regression, Bayes nets, log linear models, Perceptron-like algorithms, Gaussian processes, Bayesian techniques, probabilistic modeling techniques, regression trees, ranking algorithms, Kernel Methods, Margin based algorithms, or linear, quadratic, convex, conic or semi-definite programming techniques or any modifications or combinations of the foregoing. Further, embodiments of the present invention contemplate using machine learning algorithms developed in the future, including newly developed algorithms or modifications of the above listed learning algorithms.

In another embodiment, the learning algorithm used at step 508 attempts to minimize (directly or indirectly) the area above a receiver operator characteristic (ROC) curve (see "Model Selection via the AUC", Saharon Rosset, Proceedings of the 21$^{st}$ International Conference on Machine Learning, 2004, incorporated herein in its entirety) constructed either on the training data or on an arbitrary set of molecules real, imagined or virtual. The use of ROC curves allows the molecular properties model output at step 510 to balance trade-offs between false positive and false negative test results as part of the learning process.

In another embodiment of the invention, the learning algorithm is an arbitrary algorithm that attempts to minimize (directly or indirectly) any cost function that relates to predictions made by the model regarding the relative ordering of molecules. Those skilled in the art will recognize that both currently known and novel learning algorithms configured to process training examples in the form of a PPO of ranked pairs may be used at step 508, and are contemplated by the invention.

Figure 6:
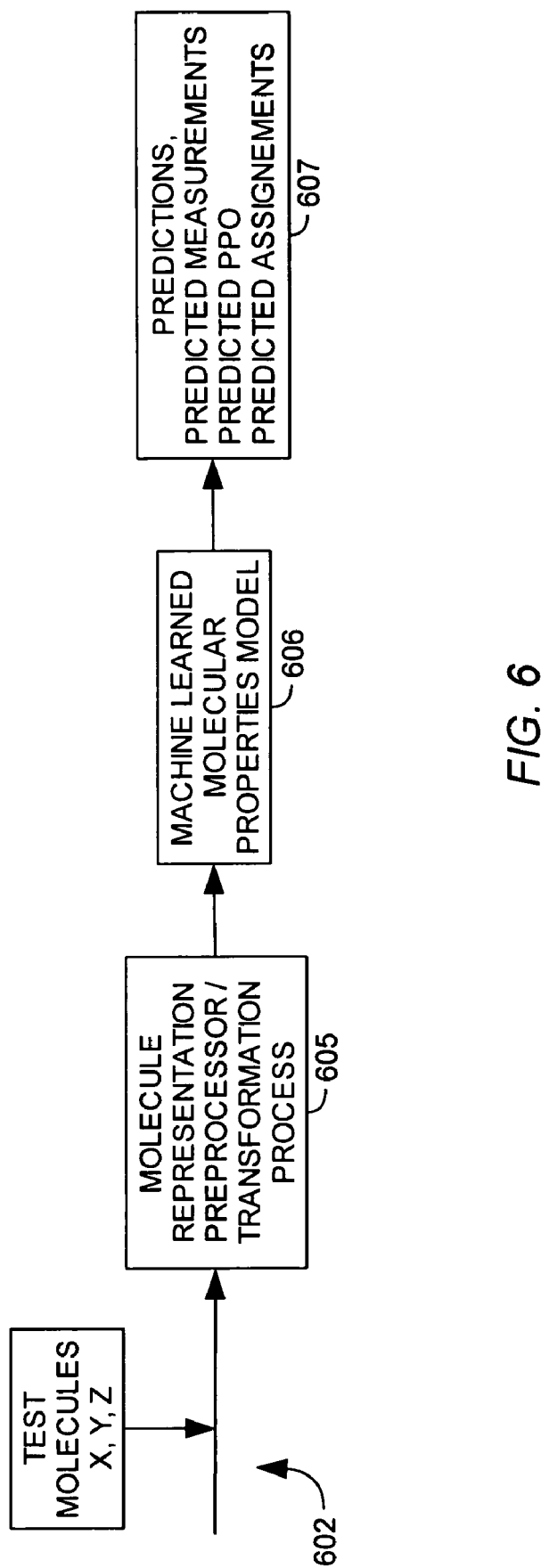
FIG. 6 illustrates a block diagram of data flow through a molecular properties model trained to generate predictions about an arbitrary molecule, according to one embodiment of the invention.

FIG. 6 illustrates a block diagram of data flow through a molecular properties model 606, configured to generate a prediction for an arbitrary molecule, according to one embodiment of the invention. The prediction 607 may provide a predicted measurement value for the property of interest, or may assign a label such as "active" or "inactive" to the molecule. Alternatively, in one embodiment, the prediction 607 may predict a PPO of ranked pairs for the molecules provided to molecular properties model 606.

Illustratively, the block diagram 600 shows input molecules 602, data preprocessor 605, molecular properties model 606, and predictions 607. In one embodiment, preprocessor 605 constructs a representation of each molecule for which a prediction 607 is desired. For example, the transformation process used to create molecule descriptions as part of step 506 from FIG. 5 may be used. The transformed representations are then provided to molecular properties model

606. The molecular properties model 606 then outputs a prediction 607 for the input molecules 602.

Embodiments of the present invention may make use of training data that is not in a ranked form. In particular, embodiments of the present invention may make use of data that is not represented as a PPO. Further, embodiments of the invention may construct molecular properties models by optimizing a loss function that considers the relative ordering of the molecules in the training data. For example, embodiments of the invention may use training data that represents molecules as being either active or inactive for a property of interest, or may construct a molecular properties model by optimizing a function of the rank order assigned to the molecules. An example of such a function is the area above (below) the ROC curve. Similarly, embodiments of the invention may use training data that represents the molecular property of interest as a continuous value. Such embodiments attempt to optimize a loss function of the rank order assigned to said molecules. Such a loss function penalizes incorrectly ordered molecules. Those skilled in the art will recognize that learning algorithms that optimize a loss function of the rank order of a set of molecules (atoms or bonds) are implicitly considering the training data as a PPO.

Embodiments of the present invention may be used to construct molecular properties models when the training data is biased, or when the optimal trade-off between false positives and false negatives is unknown a priori. The invention constructs a ranking model by generating ranking data (e.g. a PPO) or by optimizing a function of the rank ordering of molecules in the training set. Subsequent to model construction a classification model may be obtained by determining a threshold value or cutoff molecule. Molecules that score above the threshold, or rank above the cutoff molecule are considered in one class, the remaining molecules are considered in the other class. The threshold value or cutoff molecule may be determined a posteriori based on information that becomes available, e.g., a specification of the optimal trade-off between false positives and false negatives.

Molecules predicted to exhibit the property of interest, predicted to have a high measurement value for the property of interest, or otherwise identified by molecular properties models constructed by the present invention, may be identified for further investigation, including experimentation carried out in the laboratory or using additional computer simulation techniques. Given the current availability of data transport mechanisms, predictions generated for a test molecule at one location may be transported to other locations using well known data storage and transmission techniques. And predictions may be verified experimentally at the other locations. For example, a computer system may be located in one country and configured to generate predictions about the property of interest for a selected group of molecules, this data may be then be transported (or transmitted) to another location, or even another country, where it may be the subject of further investigation, e.g., laboratory confirmation of the prediction or further computer-based simulations.

While the foregoing is directed to embodiments of the present invention, other and further embodiments of the invention may be devised without departing from the basic scope thereof, and the scope thereof is determined by the claims that follow.

What is claimed is:

1. A method for training a molecular properties model, comprising:

ranking a training set of property measurements for a plurality of molecules, wherein each measurement assigns a value for a property of interest relative to a single molecule;

generating a representation of the molecules included in the training set that is appropriate for a selected machine learning algorithm;

providing the training set to a selected machine learning algorithm that optimizes a function of the rank order of the molecules in the training set relative to the property of interest, wherein, for at least two molecules in said training set, said function penalizes incorrectly ordered molecules when said function is evaluated on said at least two molecules;

executing on a computer system the machine learning algorithm to generate a trained molecular properties model;

selecting at least one additional molecule;

generating a representation of the at least one additional molecule appropriate for the molecular properties model;

generating on a computer system and with the molecular properties model a prediction about the at least one additional molecule regarding the property of interest; and determining the accuracy of the prediction for the at least one additional molecule by performing laboratory experimentation using a physically realized sample of the test molecule.

2. The method of claim 1, wherein the molecular properties model generates predictions related to a property of interest selected from at least one of a pharmacokinetic property, pharmacodynamic property, physiological activity, pharmacological activity, toxicity, selectivity, binding affinity, pKa, a property of a specific atom or bond in a molecule, melting point, solubility, a membrane permeability, or a force-field parameter.

3. The method of claim 1, wherein the selected machine learning algorithm comprises a Boosting algorithm, RankBoost algorithm, Alternating Decision Trees algorithm, Support Vector Machines algorithm, a Perceptron algorithm, Winnow, a Hedge Algorithm, decision trees, neural networks, genetic algorithms or genetic programming.

4. The method of claim 1, wherein the selected machine learning algorithm is configured to minimize, either directly or indirectly, an area above, or below, a receiver operator characteristic curve.

5. The method of claim 1, further comprising, determining an accuracy of the prediction for the additional molecule by performing a research study using physical samples of the additional molecule.

6. The method of claim 1, wherein generating the representation of the molecules included in the training set comprises: generating a vector representation of the molecules, wherein the vector representation is configured to encode the structure the molecules included the training set; or comprises generating an n-point pharmacophore representation of the molecules included in the training set.

7. The method of claim 1, wherein a threshold value or cutoff molecule is selected for the molecular properties model.

8. The method of claim 1, wherein the step of generating a representation of the at least one additional molecules comprises generating a representation of at least two or more additional molecules, and wherein the prediction comprises a ranked ordering of the two or more additional molecules, relative to one another and to the property of interest.

9. The method of claim 1, wherein at least two of the molecules in the training set are alternative representations of the same physical molecule and the property of interest is a property of said alternative representations.

10. A physical computer-storage medium containing a program which, when executed by a processor, performs a method for training a molecular properties model, comprising:
  receiving a ranked training set of property measurements for a plurality of molecules, wherein each measurement assigns a value for a property of interest relative to a single molecule;
  generating a representation of the molecules included in the training set that is appropriate for a selected machine learning algorithm;
  providing the training set to a selected machine learning algorithm that optimizes a function of the rank order of the molecules in the training set relative to the property of interest, wherein, for at least two molecules in said training set, said function penalizes incorrectly ordered molecules when said function is evaluated on said at least two molecules;
  executing the machine learning algorithm to generate a trained molecular properties model;
  selecting at least one additional molecule;
  generating a representation of the at least one additional molecule appropriate for the molecular properties model; and
  generating with the molecular properties model a prediction about the at least one additional molecule regarding the property of interest.

11. The method of claim 1, comprising the additional step that the accuracy of the prediction for the at least one additional molecule is determined by performing a computational simulation configured to model the property of interest for the additional molecule.

12. The method of claim 1, further comprising using the predictions regarding the additional molecules to identify at least one molecule; and physically realizing said molecule.

13. The method of claim 1, wherein the set of property measurements include virtual data.

14. The method of claim 1, wherein the plurality of molecules include virtual molecule(s).

15. The method of claim 1, wherein the at least one additional molecule includes at least one virtual molecule.

16. The method of claim 1, wherein molecules in the training set are weighted, and the machine learning algorithm is configured to minimize a function of the weighted rank order of the molecules.

17. The method of claim 1, wherein the providing the training set to a selected machine learning algorithm comprises constructing a pseudo-partial ordering of molecules, wherein the pseudo-partial ordering includes at least a representation of a first and second molecule, ordered relative to one another and the property of interest.

18. The method of claim 17, wherein the molecular properties model generates predictions related to a property of interest selected from at least one of a pharmacokinetic property, pharmacodynamic property, physiological activity, pharmacological activity, toxicity, selectivity, binding affinity, pKa, a property of a specific atom or bond in a molecule, melting point, solubility, a membrane permeability, or a force-field parameter.

19. The method of claim 17, wherein the selected machine learning algorithm comprises a classification learning algorithm.

20. The method of claim 17, wherein the selected machine learning algorithm comprises a kernel based learning algorithm.

21. The method of claim 17, wherein the selected machine learning algorithm comprises a Boosting algorithm, RankBoost algorithm, Alternating Decision Trees algorithm, Support Vector Machines algorithm, a Perceptron algorithm, Winnow, a Hedge Algorithm, decision trees, neural networks, genetic algorithms or genetic programming.

22. The method of claim 17, wherein the selected machine learning algorithm is configured to minimize, either directly or indirectly, an area above, or below, a receiver operator characteristic curve.

23. The method of claim 17, wherein the selected machine learning algorithm is configured to minimize, either directly or indirectly, a function of the rank ordering of molecules in the pseudo partial ordering.

24. The method of claim 17, further comprising, determining an accuracy of the prediction for the additional molecule by performing a research study using physical samples of the additional molecule.

25. The method of claim 17, wherein constructing the representation of the molecules included in the pseudo partial ordering of molecules comprises: generating a vector representation of the molecules, wherein the vector representation is configured to encode the structure of the molecules included the pseudo-partial ordering; or comprises generating an n-point pharmacophore representation of the molecules included in the pseudo-partial ordering.

26. The method of claim 17, wherein a threshold value or cutoff molecule is selected for the molecular proprieties model.

27. The method of claim 17, wherein the at least one additional molecule comprises two or more additional molecules, and wherein the prediction comprises a ranked ordering of the two or more additional molecules, relative to one another and to the property of interest.

28. The method of claim 17, wherein at least two of the molecules in the training set are alternative representations of the same physical molecule and the property of interest is a property of the alternative representations.

* * * * *